United States Patent [19]

Oeckl et al.

[11] Patent Number: 4,560,694
[45] Date of Patent: Dec. 24, 1985

[54] FUNGICIDAL ALKYLENE(CYCLOALKYLENE)-BIS-HETEROCYCLYL-BIGUANIDES

[75] Inventors: Siegfried Oeckl, Bergisch-Gladbach; Hans-Georg Schmitt, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 496,715

[22] Filed: May 20, 1983

[30] Foreign Application Priority Data

Jun. 4, 1982 [DE]  Fed. Rep. of Germany ....... 3221139
Jan. 29, 1983 [DE] Fed. Rep. of Germany ....... 3303064

[51] Int. Cl.⁴ .............. A01N 43/50; A01N 43/64; C07D 233/61; C07D 249/08
[52] U.S. Cl. ................... 514/359; 548/251; 548/252; 548/254; 548/255; 548/257; 548/259; 548/260; 548/262; 548/263; 548/265; 548/327; 548/328; 548/336; 548/374; 514/381; 514/383; 514/384; 514/394; 514/395; 514/397; 514/406; 514/407
[58] Field of Search .......... 548/251, 252, 254, 257, 548/259, 260, 255, 263, 265, 262, 327, 328, 336, 374; 424/269, 273 R, 273 B, 273 P; 514/359, 381, 383, 384, 394, 395, 397, 406, 407

[56] References Cited

U.S. PATENT DOCUMENTS 3,150,148  9/1964  Dulin et al. .................... 548/378
4,062,967 12/1977  Durant et al. ................... 548/374

FOREIGN PATENT DOCUMENTS 478802  9/1969  Switzerland .................... 548/378

OTHER PUBLICATIONS

Verlag Chemie, Weinheim/Bergstr.; Dentalchemie bis Erdolverarbeitung; Band 10; p. 54, (1976).

*Primary Examiner*—Richard A. Schwartz
*Assistant Examiner*—Kurt G. Briscoe
*Attorney, Agent, or Firm*—Sprung, Horn, Kramer & Woods

[57] ABSTRACT

Alkylene(cycloalkylene)-bis-heterocyclyl-biguanides of the formula

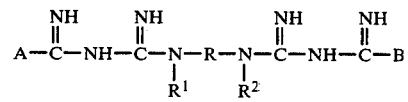

in which

A and B each independently is a nitrogen-containing heterocyclic radical which is linked via a nitrogen atom, R is an optionally alkyl-substituted cycloalkylene radical, or an alkylene radical which is optionally substituted by cycloalkylene, bicycloalkylene, tricycloalkylene, oxygen, sulphur or the $NR^3$ group, $R^1$ and $R^2$ each independently is hydrogen, alkyl or optionally substituted aralkyl, or $R^1$ and $R^2$ together with the two nitrogen atoms on which they are located and R form a heterocyclic ring, and $R^3$ is hydrogen, alkyl or optionally substituted aralkyl, or salts thereof which possess fungicidal activity.

8 Claims, No Drawings

FUNGICIDAL ALKYLENE(CYCLOALKYLENE)-BIS-HETEROCYCLYL-BIGUANIDES

The present invention relates to new alkylene-(cycloalkylene)-bis-heterocyclyl-biguanides, a process for their preparation and their use as agents for combating pests.

It has already been disclosed that alkylene-bis-arylbiguanides, such as, for example, chlorhexidine of the formula

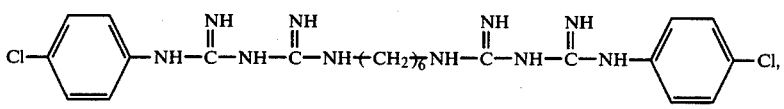

are used for disinfection purposes in the industrial field and in the human field (compare Ullmann's Encyclopä die der technischen Chemie (Ullman's Encyclopaedia of Industrial Chemistry), 4th Edition, Volume 10, page 54, Verlag Chemie Weinheim 1975). Nothing is known of an action against pests in plant protection.

It has also been known for a long time that N-sulphenylated dicarboxylic acid imides, such as N-trichloromethylthio-tetrahydrophthalimide, have a fungicidal activity (compare German Pat. No. 1,193,498).

New alkylene(cycloalkylene)-bis-heterocyclylbiguanides of the formula (I)

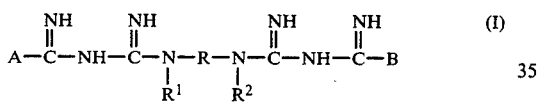

in which

A and B are identical or different and represent heterocyclic radicals which are linked via nitrogen and can optionally be substituted, R represents optionally alkyl-substituted cycloalkylene, or alkylene, it being possible for the alkylene chain to be interrupted at one or more places by cycloalkylene, bicycloalkylene or tricycloalkylene groups which are optionally mono- or poly-substituted by alkyl, or by oxygen atoms, sulphur atoms or the group NR$^3$, R$^1$ and R$^2$ are identical or different and represent hydrogen, alkyl or optionally substituted aralkyl, or R$^1$ and R$^2$, including the two nitrogen atoms on which they are located and the alkylene radical, form a heterocyclic ring, and R$^3$ represents hydrogen, alkyl or optionally substituted aralkyl, have been found.

It has furthermore been found that the alkylene-(cyclalkylene)-bis-heterocyclyl-biguanides of the formula (I)

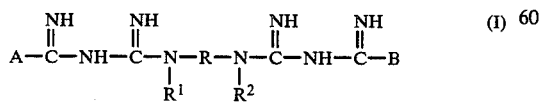

in which

A and B are identical or different and represent heterocyclic radicals which are linked via nitrogen and can optionally be substituted, R represents optionally alkyl-substituted cycloalkylene, or alkylene, it being possible for the alkylene chain to be interrupted at one or more places by cycloalkylene, bicycloalkylene or tricycloalkylene groups which are optionally mono- or poly-substituted by alkyl, or by oxygen atoms, sulphur atoms or the group NR$^3$, R$^1$ and R$^2$ are identical or different and represent hydrogen, alkyl or optionally substituted arylalkyl, or R$^1$ and R$^2$, including the two nitrogen atoms on which they are located and the alkylene radical, form a heterocyclic ring, and R$^3$ represents hydrogen, alkyl or optionally substituted arylalkyl, are obtained by a process in which (a) in the case where A and B are identical, alkylene-bis-dicyanodiamides of the formula (II)

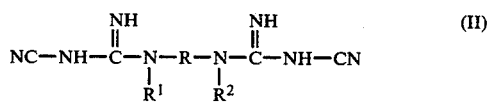

in which R, R$^1$ and R$^2$ have the abovementioned meanings, are reacted with a heterocyclic compound of the formula

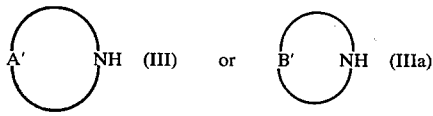

in which

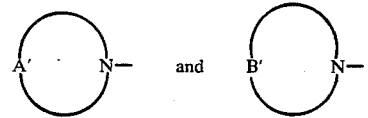

have the abovementioned meanings of A and B, as free compounds or in salt form, if appropriate in a solvent or diluent, at temperatures between 50° and 200° C., or (b) in the case where A and B are different, alkylene-bis-dicyanodiamides of the formula (II) are reacted with 1 mol of a heterocyclic compound of the formula (III) and then with 1 mol of the heterocyclic compound of the formula (IIIa), if appropriate in a solvent or diluent, at temperatures of 50° to 200° C.

The new alkylene(cycloalkylene)-bis-heterocyclyl-biguanides have powerful fungicidal properties. Surprisingly, the compounds of the formula (I) according to the invention exhibit a better fungicidal activity than N-trichloromethylthio-tetrahydrophthalimide, which is known from the prior art. The substances according to the invention thus represent an enrichment of the art.

The formula (I) provides a general definition of the alkylene(cycloalkylene)-bis-heterocyclyl-biguanides according to the invention. Preferably, in this formula, A and B represent identical or different 5-membered or 6-membered rings, which are optionally benzo-fused, are linked via nitrogen, are optionally interrupted by further hetero-atoms and are optionally mono- or poly-substituted by identical or different substituents. Possible substituents are: halogen, nitro, alkyl with 1 to 18 carbon atoms, alkylthio with 1 to 10 carbon atoms, and aryl with 6 to 10 carbon atoms which is optionally mono-, di-, tri-, tetra-, penta- or hexa-substituted by identical or different substituents from the group comprising halogen, alkyl with 1 to 4 carbon atoms and halogenoalkyl with 1 to 3 carbon atoms and up to five halogen atoms. The fused-on benzene ring can be optionally mono-, di-, tri- or tetra-substituted by the substituents listed in the case of the heterocyclic radicals.

R represents cycloalkyl which has 5 to 9 carbon atoms in the ring and is optionally mono- or poly-substituted by identical or different alkyl groups with 1 to 6 carbon atoms, or represents straight-chain or branched alkylene with 1 to 20 carbon atoms, the alkylene chain optionally being mono- or poly-substituted by cycloalkylene radicals with 5 to 7 carbon atoms in the ring, by bicyclo- or tricyclo-alkylene radicals with 6 to 18 carbon atoms in the rings, it being possible for the rings to be mono- or poly-substituted by lower alkyl with 1 to 4 carbon atoms, or by oxygen or sulphur atoms or by the group $NR^3$, $R^1$ and $R^2$ are identical or different and represent hydrogen, alkyl with 1 to 20 carbon atoms or aralkyl with 6 to 10 carbon atoms in the aryl part and 1 to 6 carbon atoms in the alkyl part, it being possible for the aryl part to be mono-, di-, tri-, tetra- or penta-substituted by identical or different substituents from the group comprising alkyl with 1 to 6 carbon atoms and halogen, or $R^1$ and $R^2$, including the alkylene radical and the nitrogen atoms on which the radicals $R^1$ and $R^2$ are located, represent a heterocyclic ring with 5 to 10 ring members, and $R^3$ represents hydrogen, alkyl with 1 to 6 carbon atoms or optionally substituted aralkyl with 6 to 10 carbon atoms in the aryl part and 1 to 6 carbon atoms in the alkyl part, it being possible for the aryl part to be mono-, di-, tri-, tetra- or penta-substituted by identical or different substituents from the group comprising alkyl with 1 to 6 carbon atoms and halogen.

Particularly preferred compounds of the formula (I) are those in which

A and B are identical and represent a triazole, such as 1,2,4-triazole, 1,3,4-triazole or 1,2,3-triazole, tetrazole, pyrazole or imidazole radical which is optionally mono-, di- or tri-substituted by identical or different substituents from the group comprising halogen, such as chlorine, fluorine and bromine, nitro, alkyl with 1 to 9 carbon atoms, such as methyl, ethyl, n-propyl, iso-propyl, n-butyl, iso-butyl, tert.-butyl, sec.-butyl, pentyl, hexyl, octyl and nonyl, alkylthio with 1 to 4 carbon atoms, such as methylthio, ethylthio, n-propylthio, isopropylthio, n-butylthio, iso-butylthio, sec.-butylthio and tert.-butylthio or phenyl, furthermore benzotriazole and benzimidazole radicals, the fused-on benzene ring being optionally mono-, di-, tri- or tetra-substituted by identical or different substituents from the group comprising halogen, such as fluorine, chlorine and bromine, nitro, alkyl with 1 to 6 carbon atoms, such as methyl, ethyl, n-propyl, iso-propyl, n-butyl, iso-butyl, sec.-butyl, tert.-butyl, pentyl, and hexyl, or alkylthio with 1 to 4 carbon atoms, such as methylthio, ethylthio, n-propylthio, iso-propylthio, n-butylthio, sec.-butylthio, isobutylthio and tert.-butylthio, or phenyl optionally substituted by methyl, ethyl, propyl, fluorine, chlorine, trifluormethyl or difluorchloromethyl, R represents cycloalkylene with 5 to 7 carbon atoms in the ring, such as cyclopentylene, cyclohexylene and cycloheptylene, the rings optionally being mono- or poly-substituted by alkyl with 1 to 4 carbon atoms, such as methyl, ethyl, n-propyl, iso-propyl, n-butyl, iso-butyl, sec.-butyl or tert.-butyl, straight-chain or branched alkylene with 1 to 12 carbon atoms, such as methylene, ethylene, iso-propylene, n-propylene, b-butylene, iso-butylene, sec.-butylene, tetramethylene, pentamethylene, hexamethylene, heptamethylene, octamethylene, nonamethylene, decamethylene, 2,5-dimethylhexylene, 3,5,5-trimethyl-hexylene or 1-methylenethylene, or alkylene radicals which have 1 to 4 carbon atoms in each alkylene radical and are mono- or polysubstituted by cycloalkylene or bi- or tri-cycloalkyene with 5 to 12 carbon atoms in the ring system, such as 1,3,3-trimethyl-cyclohexylmethylene, dicyclohexylenemethane, 2,2'-dimethyldicyclohexylenemethane or bismethylenetricyclodecane, or alkylene radicals with 1 to 6 carbon atoms which are optionally interrupted in one or more places by oxygen, sulphur or $NR^3$, such as N,N'-bisethyleneethylenediamine, tetraethylene-triamine, pentaethylenetetramine, dipropyleneamine, tripropyleneamine or 1,4-butanediol-bispropylene ether, and $R^1$ and $R^2$ are identical or differrent and represent hydrogen, alkyl with 1 to 10 carbon atoms, such as methyl, ethyl, n-propyl, iso-propyl, n-butyl, sec.-butyl, iso-butyl, tert.-butyl, pentyl, hexyl, heptyl, octyl, nonyl or decyl, or aralkyl, such as phenethyl or benzyl, it being possible for the aryl radical to be mono-, di-, tri-, tetra- or penta-substituted by identical or different substituents from the group comprising alkyl with 1 to 4 carbon atoms, such as methyl, ethyl, n-propyl, iso-propyl, n-butyl, sec.-butyl, iso-butyl and tert.-butyl, and halogen, such as fluorine, chlorine, bromine and iodine, or $R^1$ and $R^2$, including the alkylene radical and the nitrogen atoms on which the radicals $R^1$ and $R^2$ are located, form a heterocyclic ring with 5 to 10 ring members, and $R^3$ represents hydrogen, alkyl with 1 to 4 carbon atoms, such as methyl, ethyl, n-propyl, iso-propyl, n-butyl, sec.-butyl, iso-butyl and tert.-butyl, or aralkyl, such as benzyl or phenethyl, it being possible for the aryl radical to be substituted by alkyl with 1 to 4 carbon atoms and/or fluorine, chlorine, bromine or iodine.

If, for example, hexamethylene-bis-dicyanodiamide and 1,2,4-triazole are used as starting compounds in process variant (a) according to the invention, the course of the reaction can be represented by the following equation:

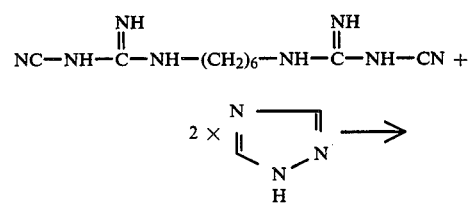

-continued

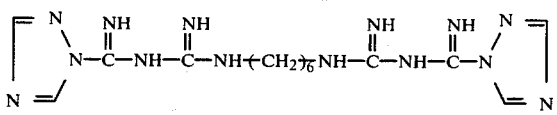

If, for example, tetramethylene-bis-dicyanodiamide and 1,2,4-triazole are used as starting materials in the first step of process variant (b) according to the invention and benzimidazole is used as the starting materials in the second step, the course of the reaction can be represented by the following equation:

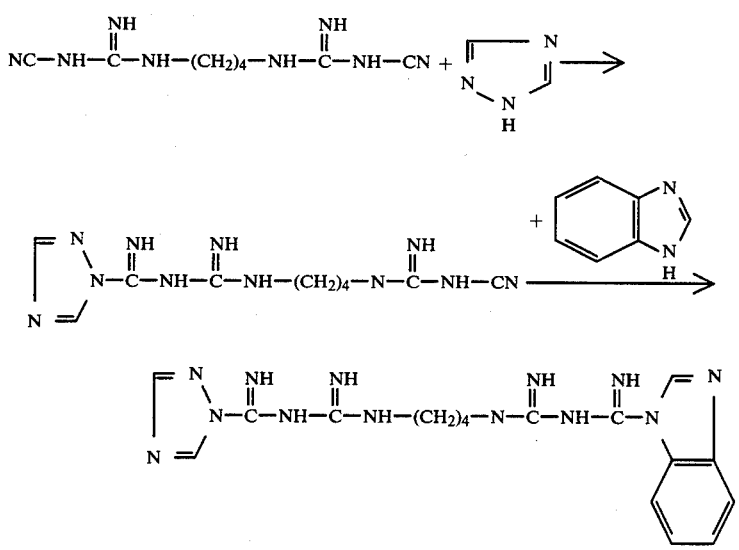

Most of the heterocyclic compounds of the formula III or IIIa, or the salts thereof, which are to be used as starting substances in carrying out process variants (a) and (b) according to the invention are known, or they can be prepared by known processes.

Most of the alkylene-bis-dicyanodiamides of the formula (II) which are also to be used as starting substances in variant (a) are known, or they can be prepared by known processes (compare British Pat. Nos. 631,878 and 702,268).

Possible diluents or solvents for the reaction, according to the invention, in process variants (a) and (b) are organic solvents. These include, preferably, alcohols, such as methanol, ethanol, iso-propanol, n-propanol, n-butanol, iso-butanol, amyl alcohol, cyclohexanol and phenol; glycols and glycol ethers, such as ethylene glycol, ethylene glycol monoalkyl and dialkyl ethers and diethylene glycol; as well as hydrocarbons and halogenohydrocarbons, such as toluene, chloroaromatics and paraffin oil; carboxylic acids, such as formic acid, acetic acid and propionic acid, and in addition also water.

The reaction is preferably carried out without a solvent, above the melting point of the reaction mixture.

The reaction can be carried out under normal, reduced or increased pressure. It is preferably carried out under normal pressure.

The reaction temperatures can be varied within a substantial range in carrying out the process according to the invention. In general, the reaction is carried out between 50° C. and 200° C., preferably between 100° C. and 170° C.

The course of the reaction can easily be seen by the diminution of the CN band in the IR spectrum, and accordingly the end of the reaction manifests itself by the disappearance of the CN band, but the reaction can, of course, also be interrupted earlier, for example if the thermal stability of the starting materials or end products to heat is not sufficient to achieve 100% conversion without a loss in yield.

Working up and purification are carried out by customary methods, such as, for example, comminution, solution, filtration, evaporation and recrystallization.

In a preferred embodiment, the heterocyclic compounds are employed in salt form, preferably with physiologically acceptable acids.

Salts of either organic or inorganic acids can be used, such as, for example, those of formic acid, acetic acid, hydrochloric acid, sulphuric acid or phosphoric acid. The hydrochlorides are preferably used. The salt formation can also be carried out in a process step directly following the reaction.

The active compounds according to the invention exhibit a powerful microbicidal action and can be employed in practice for combating undesired microorganisms. The active compounds are suitable for use as plant protection agents.

Thus, for example, fungicidal agents can be employed in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

In plant protection, the active compounds according to the invention can be particularly successfully employed for combating species of Botrytis, against fungal pathogens in cereals, such as, for example, against species of Erysiphe, Septoria, Puccinia and Pyrenophora, and also against Pellicularia in rice.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of inorganic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules and latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azole, and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.00001 to 0.02%, are required at the place of action.

PREPARATION EXAMPLES

Example 1

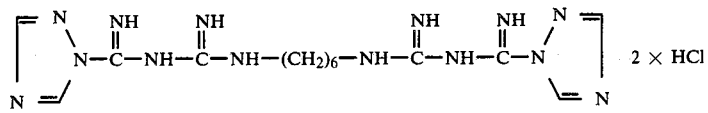

25 g (0.1 mol) of hexamethylene-bis-dicyanodiamide, 21 g (0.2 mol) of 1,2,4-triazole hydrochloride and 20 ml of water are brought to an internal temperature of 145°–150° C., while the water is distilled off. Slow stirring is continued at this temperature for 5–10 hours, until the CN band in the IR spectrum has disappeared. The clear, viscous melt is then poured out and cooled and the resinous mass form is comminuted. Without the residues which remain in the reaction vessel, a yield of 42 g (91% of theory) of hexamethylene-bis-triazol-1-yl-biguanide dihydrochloride is obtained.

Example 2

The procedure followed is as in Example 1, but 21 g (0.2 mol) of imidazole hydrochloride are used instead of the triazole. The yield is 43 g (93% of theory) of a resinous-viscous, translucent product. After recrystallization from water, flaky, brittle crystals of hexamethylene-bis-imidazol-1-yl-biguanide dihydrochloride of melting point 172°–178° C. are formed.

Example 3

13 g (0.1 mol) of 2-methyl-nitroimidazole and 10 g (0.1 mol) of 36% strength hydrochloric acid are warmed to 60° C., during which the hydrochloride of the azole is formed. 12.5 g (0.05 mol) of hexamethylene-bis-dicyanodiamide are added and water is distilled off in a weak stream of nitrogen until the internal temperature is 145°–150° C. After 5–10 hours at this temperature, the CN band has disappeared from the IR spectrum. Working up is carried out as in Example 1. The yield is 27 g (94% of theory) of resinous, readily hygroscopic hexamethylene-bis-2-methyl-nitroimidazol-1-yl-biguanide dihydrochloride.

Following the same procedure as in Example 3 the following compounds can be prepared:

| Example No. | Structure | Melting point [°C.] |
|---|---|---|
| 4 | [pyrazol-1-yl–N=C(NH)–NH–C(NH)=NH–(CH$_2$)$_3$–]$_2$ · 2HCl | 150–160 |
| 5 | [methylbenzotriazol-1-yl–C(=NH)–NH–C(=NH)–NH–(CH$_2$)$_3$–]$_2$ · 2HCl | 155–165 |
| 6 | [benzotriazol-1-yl–C(=NH)–NH–C(=NH)–NH–(CH$_2$)$_3$–]$_2$ · 2HCl | resin |
| 6 | [2-methylimidazol-1-yl–C(=NH)–NH–C(=NH)–NH–(CH$_2$)$_3$–]$_2$ · 2HCl | resin |
| 8 | [4,5-diphenylpyrimidin-1-yl–C(=NH)–NH–C(=NH)–NH–(CH$_2$)$_3$–]$_2$ · 2HCl | 187–192 |
| 9 | isophorone-diamine bis(1,2,4-triazol-1-yl-biguanide) · 2HCl | 200 |
| 10 | isophorone-diamine bis(imidazol-1-yl-biguanide) · 2HCl | resin |

| Example No. | Structure | Melting point [°C.] |
|---|---|---|
| 11 | ![structure] | resin |
| 12 | ![structure] | resin |
| 13 | ![structure] | resin |
| 14 | ![structure] | resin |
| 15 | ![structure] | resin |
| 16 | ![structure] | |
| 17 | ![structure] | |

Use Examples

In the example which follows, the compound shown below is used as the comparison substance:

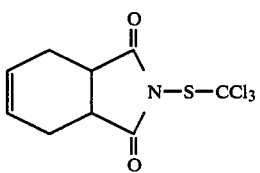

Example A

Botrytis test (beans)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 2, 1 and 3.

It will be appreciated that the instant specification and examples are set forth by way of illustration and not

We claim:

1. An alkylene(cycloalkylene)-bis-heterocyclyl biguanide of the formula

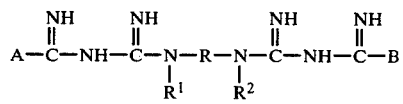

in which

A and B each independently is a triazole, tetrazole, pyrazole, imidazole, benzotriazole or benzimidazole radical which is linked via a nitrogen atom and which is optionally substituted by at least one member selected from the group consisting of halogen, nitro, alkyl with 1 to 18 carbon atoms, alkylthio with 1 to 10 carbon atoms, and aryl with 6 to 10 carbon atoms which is optionally mono-, di-, tri-, tetra-, penta- or hexa-substituted by at least one substituent selected from the group consisting of halogen, alkyl with 1 to 4 carbon atoms and halogenoalkyl with 1 to 3 carbon atoms and up to 5 halogen atoms, R is an optionally $C_{1-6}$-alkyl-substituted cycloalkylene radical with 5 to 9 carbon atoms, or a $C_{1-20}$-alkylene radical which is optionally substituted by $C_{5-7}$-cycloalkylene, $C_{6-12}$-bicycloalkylene, $C_{9-18}$-tricycloalkylene, oxygen, sulphur or the $NR^3$ group, $R^1$ and $R^2$ each independently is hydrogen, $C_{1-20}$-alkyl or aralkyl which has 6 to 10 carbon atoms in the aryl part and 1 to 6 carbon atoms in the alkyl part and is optionally substituted by $C_{1-6}$-alkyl or halogen, and $R^3$ is hydrogen, $C_{1-6}$-alkyl or optionally substituted aralkyl which has 6 to 10 carbon atoms in the aryl part and 1 to 6 carbon atoms in the alkyl part and is optionally substituted by $C_{1-6}$-alkyl or halogen, 2. An alkylene(cycloalkylene)-bis-heterocyclyl-biguanide or salt according to claim 1, in which A and B are identical, and each is a triazole, tetrazole, pyrazole or imidazole radical which is optionally substituted by halogen, nitro, alkyl with 1 to 9 carbon atoms or alkylthio with 1 to 4 carbon atoms or phenyl, or a benzotriazole or benzimidazole radical, the fused-on benzene ring being optionally substituted by halogen, nitro, alkyl with 1 to 4 carbon atoms, alkylthio with 1 to 4 carbon atoms or phenyl optionally substituted by methyl, ethyl, propyl, fluorine, chlorine, trifluoromethyl or difluorochloromethyl, R is cycloalkylene with 5 to 7 carbon atoms in the ring, the rings optionally being substituted by alkyl with 1 to 4 carbon atoms, alkylene with 1 to 12 carbon atoms, or alkylene which has 1 to 4 carbon atoms per alkylene radical and is substituted by cycloalkylene, bicycloalkylene or tricycloalkylene radicals with 5 to 12 carbon atoms in the ring system or alkylene radicals with 1 to 6 carbon atoms which are interrupted by oxygen atoms, sulphur atoms or the $NR^3$ group, $R^1$ and $R^2$ each independently is hydrogen, alkyl with 1 to 10 carbon atoms or aralkyl, the aryl radical optionally being substituted by alkyl with 1 to 4 carbon atoms or halogen, and $R^3$ is hydrogen, alkyl with 1 to 4 carbon atoms or aralkyl, the aryl radical optionally being substituted by alkyl with 1 to 4 carbon atoms, fluorine, chlorine, bromine or iodine.

3. A compound according to claim 1, wherein such compound is hexamethylene-bis-triazol-1-yl-biguanide of the formula

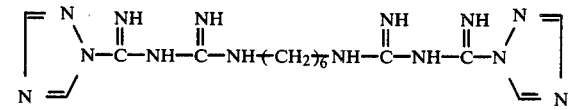

or a salt thereof.

4. A compound according to claim 1, wherein such compound is hexamethylene-bis-imidazol-1-yl-biguanide of the formula

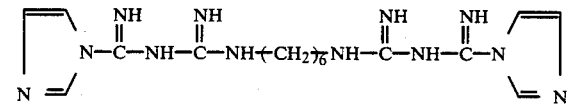

or a salt thereof.

5. A compound according to claim 1, wherein such compound is hexamethylene-bis-2-methyl-4-nitroimidazol-1-yl-biguanide of the formula

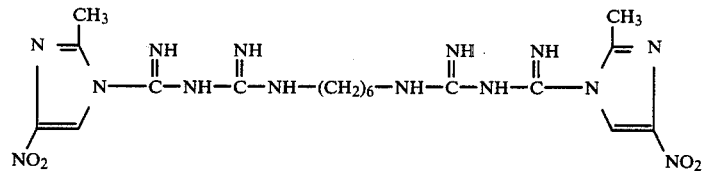

or a salt thereof.

6. A fungicidal composition comprising a fungicidally effective amount of a compound or salt according to claim 1 in admixture with a diluent.

7. A method of combating fungi which comprises applying to said fungi or to a fungus habitat a fungicidally effective amount of a compound or salt according to claim 1.

8. The method according to claim 7, wherein such compound is
hexamethylene-bis-triazol-1-yl-biguanide,
hexamethylene-bis-imidazol-1-yl-biguanide or
hexamethylene-bis-2-methyl-4-nitroimidazol-1-yl-biguanide,
or a salt thereof.

* * * * *